US012799447B2

(12) United States Patent
Takatsuka et al.

(10) Patent No.: US 12,799,447 B2
(45) Date of Patent: Nov. 17, 2026

(54) MEASUREMENT DEVICE, MEASUREMENT METHOD, AND MEASUREMENT SYSTEM

(71) Applicant: Sony Group Corporation, Tokyo (JP)

(72) Inventors: Susumu Takatsuka, Tokyo (JP); Hiroki Tetsukawa, Tokyo (JP)

(73) Assignee: Sony Group Corporation, Tokyo (JP)

( * ) Notice: Subject to any disclaimer, the term of this patent is extended or adjusted under 35 U.S.C. 154(b) by 413 days.

(21) Appl. No.: 18/256,207

(22) PCT Filed: Nov. 17, 2021

(86) PCT No.: PCT/JP2021/042189
§ 371 (c)(1),
(2) Date: Jun. 7, 2023

(87) PCT Pub. No.: WO2022/130884
PCT Pub. Date: Jun. 23, 2022

(65) Prior Publication Data

US 2024/0018461 A1 Jan. 18, 2024

(30) Foreign Application Priority Data

Dec. 18, 2020 (JP) ................................ 2020-210568

(51) Int. Cl.
*C12M 1/00* (2006.01)
*C12N 1/12* (2026.01)
*G01N 33/50* (2006.01)

(52) U.S. Cl.
CPC ............... *C12M 47/02* (2013.01); *C12N 1/12* (2013.01); *G01N 33/5029* (2013.01); *G01N 2333/44* (2013.01)

(58) Field of Classification Search
None
See application file for complete search history.

(56) References Cited

U.S. PATENT DOCUMENTS

| | | | | |
|---|---|---|---|---|
| 5,417,006 | A * | 5/1995 | Schettino | A01K 79/02 43/17.1 |
| 6,448,054 | B1 * | 9/2002 | Poznansky | A61P 9/10 424/85.1 |
| 6,448,454 | B1 | 9/2002 | Subramaniam | |
| 2012/0216601 | A1 | 8/2012 | Irimia | |

(Continued)

FOREIGN PATENT DOCUMENTS

| | | | |
|---|---|---|---|
| JP | 2013-255458 | A | 12/2013 |
| JP | 2015-000021 | A | 1/2015 |

(Continued)

OTHER PUBLICATIONS

International Search Report and Written Opinion mailed on Feb. 8, 2022, received for PCT Application PCT/JP2021/042189, filed on Nov. 17, 2021, 11 pages including English Translation.

*Primary Examiner* — Helen Zong
(74) *Attorney, Agent, or Firm* — XSENSUS, LLP

(57) ABSTRACT

A measurement device includes a stimulus control unit configured to cause a stimulus generation device to generate an external stimulus complying with a chemotaxis condition of an organism, an imaging unit configured to capture an image of a predetermined imaging range in which the external stimulus is generated, and a measurement unit configured to measure a target organism on the basis of the image captured by the imaging unit.

15 Claims, 12 Drawing Sheets

(56) References Cited

U.S. PATENT DOCUMENTS

| | | | | |
|---|---|---|---|---|
| 2013/0023041 | A1* | 1/2013 | Greenberger | A61P 7/00 435/288.3 |
| 2015/0218548 | A1 | 8/2015 | Leland | |
| 2018/0216155 | A1* | 8/2018 | Son | C40B 30/06 |
| 2020/0318077 | A1* | 10/2020 | Nahmias | C12M 21/08 |

FOREIGN PATENT DOCUMENTS

| | | | |
|---|---|---|---|
| JP | 2019-165687 | A | 10/2019 |
| JP | 2020501747 | A | 1/2020 |
| WO | 2016/103501 | A1 | 6/2016 |
| WO | 2017/159011 | A1 | 9/2017 |
| WO | 2020/021954 | A1 | 1/2020 |
| WO | WO-2020116185 | A1 | 6/2020 |

* cited by examiner

FIG. 2

| | | |
|---|---|---|
| MEASUREMENT SETTING | MEASUREMENT START CONDITION | CONDITION FOR STARTING MEASUREMENT<br>TIME or RECEPTION OF MEASUREMENT START COMMAND |
| | OPERATION TIME CHART | OPERATION SETTING OF STIMULUS GENERATION DEVICE |
| | IDENTIFICATION PROGRAM | METHOD FOR IDENTIFYING TARGET ORGANISM<br>RULE BASE or MACHINE LEARNING or INPUT/OUTPUT PARAMETERS |
| | MEASUREMENT END CONDITION | CONDITION FOR ENDING MEASUREMENT<br>TIME or RECEPTION OF MEASUREMENT END COMMAND |

FIG. 3

A

| | 0 | | | | | 5:00 | | | | | 10:00 | | | | | 15:00 | | | | | 20:00 | | | | | 25:00 | |
|---|---|---|---|---|---|---|---|---|---|---|---|---|---|---|---|---|---|---|---|---|---|---|---|---|---|---|---|
| WAVELENGTH | OFF | | | | | 420nm | | | | | OFF | | | | | 420nm | | | | | OFF | | | | | | |
| INTENSITY | OFF | | | | | $3W/m^2$ | | | | | OFF | | | | | $10W/m^2$ | | | | | OFF | | | | | | |
| TEMPERATURE | OFF | | | | | | | | | | | | | | | | | | | | | | | | | | |
| PHEROMONE | OFF | | | | | | | | | | | | | | | | | | | | | | | | | | |

B

| | 0 | | | | | 5:00 | | | | | 10:00 | | | | | 15:00 | | | | | 20:00 | | | | | 25:00 | |
|---|---|---|---|---|---|---|---|---|---|---|---|---|---|---|---|---|---|---|---|---|---|---|---|---|---|---|---|
| WAVELENGTH | OFF | 400 nm | 420 nm | 440 nm | 460 nm | 480 nm | 500 nm | 520 nm | 540 nm | 560 nm | 580 nm | 400 nm | 420 nm | 440 nm | 460 nm | 480 nm | 500 nm | 520 nm | 540 nm | 560 nm | 580 nm | 400 nm | 420 nm | 440 nm | 460 nm | 480 nm | 500 nm |
| INTENSITY | OFF | $5.0W/m^2$ | | | | | | | | | | | | | | | | | | | | | | | | | |
| TEMPERATURE | OFF | 15.0°C | | | | | | | | | | 20.0°C | | | | | | | | | | 25.0°C | | | | | |
| PHEROMONE | OFF | | | | | | | | | | | | | | | | | | | | | | | | | | |

*FIG. 5*

| | | |
|---|---|---|
| TYPE | Hemicyclops gomsoensis | |
| WAVELENGTH | ○○nm TO ○○nm | EXTERNAL STIMULUS INFORMATION |
| DIRECTION OF MOVEMENT | POSITIVE | CHEMOTACTIC RESPONSE INFORMATION |
| SPEED | ○○m/s TO ○○m/s | |
| TRAJECTORY | SPIRAL | |
| REACTION PERIOD | ○○s TO ○○s | |
| SIZE | ○○μm TO ○○μm | IMAGE INFORMATION |
| PRESENT OR ABSENCE OF TACTILE ORGAN | PRESENT | |

FIG. 7

| TYPE | NUMBER | DENSITY | AVERAGE ACTIVITY LEVEL |
|---|---|---|---|
| Hemicyclops gomsoensis | 18 | 10000 | 80% |
| Pseudocaligus fugu | 49 | 15000 | 45% |
| unknown A | 5 | 3000 | 50% |
| unknown B | 3 | 2000 | 30% |

MEASUREMENT DEVICE, MEASUREMENT METHOD, AND MEASUREMENT SYSTEM

CROSS-REFERENCE TO RELATED APPLICATIONS

The present application is based on PCT filing PCT/JP2021/042189, filed Nov. 17, 2021, which claims priority from JP 2020-210568, filed Dec. 18, 2020, the contents of each are hereby incorporated by reference.

TECHNICAL FIELD

The present technology relates to a measurement device, a measurement method, and a measurement system, and particularly relates to a technology for measuring a target organism by giving an external stimulus to an organism exhibiting chemotaxis.

BACKGROUND ART

There has been proposed a measurement device that applies excitation light having a predetermined wavelength to excite phytoplankton and measures the intensity of fluorescence emitted from the excited phytoplankton to measure the amount of the phytoplankton being present (see Patent Document 1, for example).

CITATION LIST

Patent Document

Patent Document 1: Japanese Patent Application Laid-Open No. 2019-165687

SUMMARY OF THE INVENTION

Problems to be Solved by the Invention

The measurement device described above can measure only phytoplankton excited by excitation light. Thus, to measure zooplankton or larvae of aquatic organisms, a method of collecting and testing the zooplankton or the larvae of aquatic organisms with a water sampler or a plankton net is used. However, such a method is time-consuming and cannot achieve efficient measurement.

Therefore, an object of the present technology is to efficiently measure a target organism.

Solutions to Problems

A measurement device according to the present technology includes a stimulus control unit configured to cause a stimulus generation device to generate an external stimulus complying with a chemotaxis condition of an organism, an imaging unit configured to capture an image of a predetermined imaging range in which the external stimulus is generated, and a measurement unit configured to measure a target organism on the basis of the image captured by the imaging unit.

With the configuration described above, it is possible to perform measurement on the target organism using the chemotaxis of the organism.

In the measurement device according to the present technology described above, it is conceivable that the imaging unit includes a vision sensor configured to asynchronously acquire pixel data in accordance with the amount of light incident on each of a plurality of pixels two-dimensionally arranged.

This makes it possible to read only pixel data of a pixel in which an event has occurred and measure the target organism on the basis of the pixel data.

In the measurement device according to the present technology described above, it is conceivable that the stimulus control unit causes generation of the external stimulus by which the target organism exhibits positive chemotaxis.

This makes it possible to gather the target organism in the imaging range.

In the measurement device according to the present technology described above, it is conceivable that the stimulus control unit causes generation of the external stimulus by which a non-target organism other than the target organism exhibits negative chemotaxis.

This makes it possible to exclude the non-target organism from the imaging range.

In the measurement device according to the present technology described above, it is conceivable that the stimulus control unit causes generation of the external stimulus by which a non-target organism other than the target organism exhibits negative chemotaxis and the target organism does not exhibit negative chemotaxis.

This makes it possible to reduce exclusion of the target organism from a target range while excluding the non-target organism from the imaging range.

In the measurement device according to the present technology described above, it is conceivable that the stimulus control unit causes generation of the external stimulus by which the target organism does not exhibit chemotaxis.

This makes it possible to capture an image without being affected by the external stimulus.

In the measurement device according to the present technology described above, it is conceivable that the external stimulus is light and the stimulus control unit causes application of light by which the target organism does not exhibit chemotaxis.

This makes it possible to measure the target organism in a state where it does not exhibit running performance even in a dark external environment.

In the measurement device according to the present technology described above, it is conceivable that the imaging unit captures the image while being moved along a predetermined direction.

This enables wide-range measurement.

In the measurement device according to the present technology described above, it is conceivable that the measurement unit derives information based on a behavior performed by the target organism in exhibiting chemotaxis on the basis of the image captured by the imaging unit, to specify the target organism on the basis of the information.

This makes it possible to measure an organism that exhibits chemotaxis.

In the measurement device according to the present technology described above, it is conceivable that the measurement unit derives at least one of the number, the density, or the average activity level of the target organism.

This makes it possible to measure the actual status of the target organism.

In the measurement device according to the present technology described above, it is conceivable that the imaging unit includes the vision sensor and an imaging sensor configured to capture images at regular intervals in accordance with a frame rate.

This makes it possible to measure the target organism using one or both of the images captured by the vision sensor and the imaging sensor.

In the measurement device according to the present technology described above, it is conceivable that the stimulus control unit causes the stimulus generation device to apply light having a specific wavelength and intensity, or generate heat.

This makes it possible to measure the target organism using chemotaxis of an organism that exhibits running performance or thermotaxis.

In the measurement device according to the present technology described above, it is conceivable that the stimulus control unit causes the stimulus generation device to emit a specific substance.

This makes it possible to measure an organism that exhibits chemotaxis in response to the specific substance.

A measurement method according to the present technology described above includes causing a stimulus generation device to generate an external stimulus complying with a chemotaxis condition of an organism, capturing an image of a predetermined imaging range to which the external stimulus is output, and measuring a target organism on the basis of the captured image.

Also with such a measurement method, effects similar to those produced by the measurement device according to the present technology described above can be produced.

A measurement system according to the present technology described above includes a stimulus generation device configured to generate an external stimulus complying with a chemotaxis condition of an organism, a stimulus control unit configured to cause the stimulus generation device to generate the external stimulus, an imaging unit configured to capture an image of a predetermined imaging range to which the external stimulus is output, and a measurement unit configured to measure the target organism on the basis of the image captured by the imaging unit.

Also with such a measurement system, effects similar to those produced by the measurement device according to the present technology described above can be produced.

BRIEF DESCRIPTION OF DRAWINGS

FIG. 2 is a view for explaining an example of measurement setting.

FIG. 3 is a view for explaining an example of an operation time chart.

FIG. 5 is a view for explaining definition information about a target organism.

FIG. 7 is a view for explaining an example of an identification result.

MODE FOR CARRYING OUT THE INVENTION

Hereinafter, an embodiment will be described in the following order.

<1. Configuration of measurement system>
<2. Measurement process>
<3. Use examples>
[3-1. First use example]
[3-2. Second use example]
[3-3. Third use example]
[3-4. Fourth use example]
<4. Specific examples>
[4-1. First specific example]
[4-2. Second specific example]
[4-3. Third specific example]
<5. Another example of configuration of measurement system>
<6. Conclusion>
<7. Present technology>

1. Configuration of Measurement System

First, a configuration of a measurement system 1 as an embodiment according to the present technology will be described.

The measurement system 1 is a system that performs measurement on a target organism being measured using, for example, the chemotaxis of a microorganism contained in seawater, an organism flying in the air, and the like. The measurement here is a concept including at least one of specification of the type, the number, the activity level, the density, or the characteristic of a target organism, or recording or storage of a captured image of a target organism. Furthermore, a target organism is not limited to an organism exhibiting chemotaxis, and includes an organism not exhibiting chemotaxis.

Here, chemotaxis is an innate behavior performed by an organism in response to a directional external stimulus. Examples of an external stimulus include light, pressure, gravity, a chemical substance (pheromone), electricity, vibration, temperature, contact, and the like. Then, for example, chemotaxis in response to light is referred to as running performance, and chemotaxis in response to temperature is referred to as thermotaxis. Furthermore, movement in a direction toward a source of an external stimulus is referred to as positive chemotaxis, and movement in a direction away from a source of an external stimulus is referred to as negative chemotaxis.

For example, a protozoa flagellate, the genus Euglena, moves toward a light source upon exposure to light. In this example, it can be said that a directional external stimulus is light, and the genus Euglena exhibits positive running performance.

Furthermore, when placed in an environment with a temperature gradient, a nematode moves toward a temperature field (about 25° C.) appropriate for the nematode. In this example, it can be said that a directional external stimulus is a temperature, and a nematode exhibits thermotaxis.

As described above, it is known that certain organisms exhibit chemotaxis. The measurement system 1 performs measurement on a target organism using the chemotaxis of such organisms. Organisms exhibiting chemotaxis are found in both plants and animals. Thus, the measurement system 1 can perform measurement concerning a target organism irrespective of whether the target organism is an animal or a plant.

Figure 1:
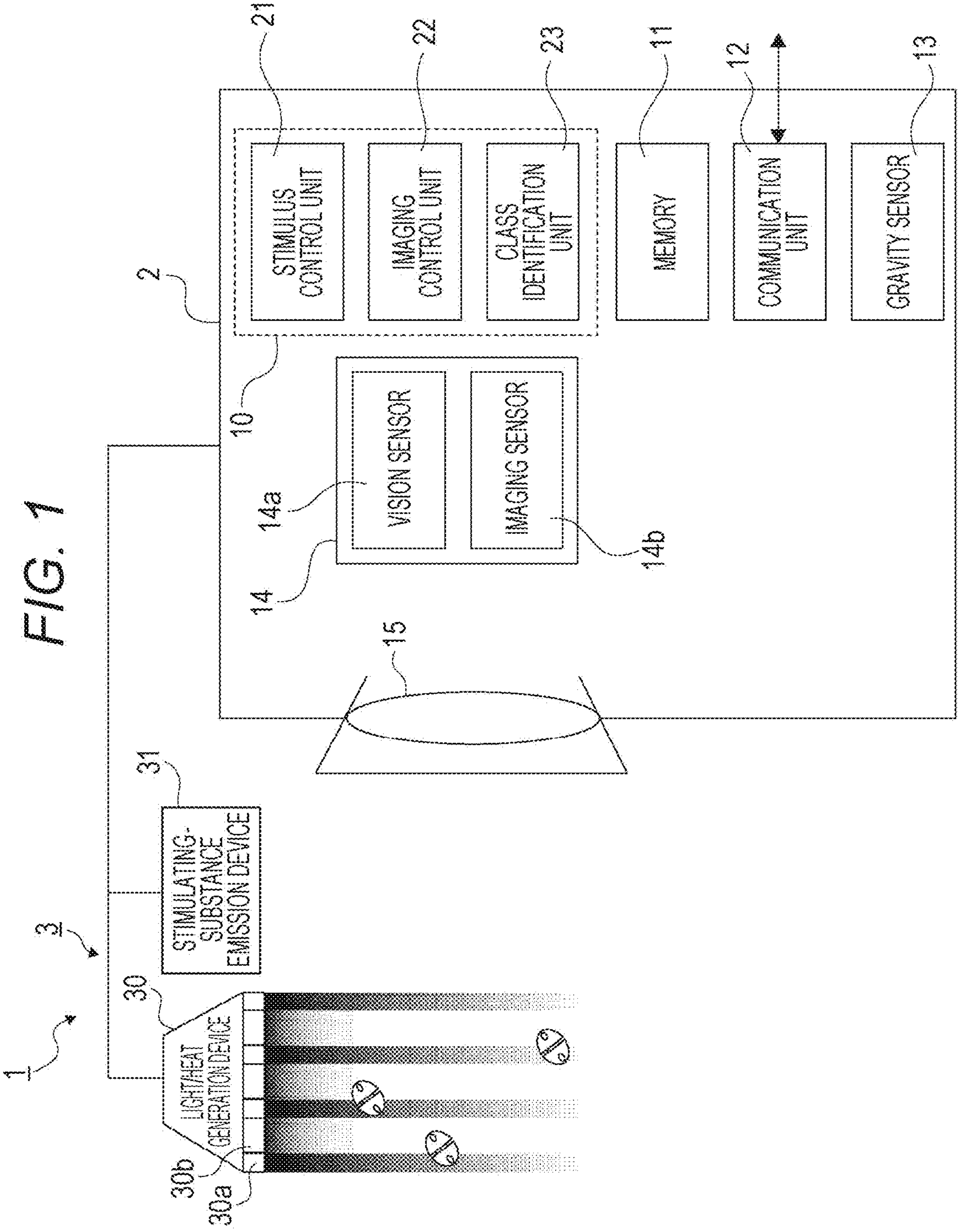
FIG. 1 is a view for explaining a configuration of a measurement system according to an embodiment.

FIG. 1 is a view for explaining a configuration of the measurement system 1 according to the embodiment. As illustrated in FIG. 1, the measurement system 1 includes a measurement device 2 and a stimulus generation device 3.

The measurement device 2 is a device that appropriately controls each device (the measurement device 2 and the stimulus generation device 3) of the measurement system 1 and performs measurement on a target organism using the chemotaxis of an organism. The measurement device 2 includes a control unit 10, a memory 11, a communication unit 12, a gravity sensor 13, an imaging unit 14, and a lens 15.

The control unit 10 includes, for example, a microcomputer including a central processing unit (CPU), a read only memory (ROM), and a random access memory (RAM), and performs overall control of the measurement system 1. In the present embodiment, the control unit 10 functions as a stimulus control unit 21, an imaging control unit 22, and a class identification unit 23. Note that the stimulus control unit 21, the imaging control unit 22, and the class identification unit 23 will be described later in detail.

Furthermore, the control unit 10 performs a process of reading data stored in the memory 11, a process of storing data into the memory 11, and transmission and reception of various data to/from an external device via the communication unit 12.

The memory 11 includes a nonvolatile memory. The communication unit 12 performs wired or wireless data communication to/from an external device. The gravity sensor 13 detects a gravitational acceleration (direction of gravity) and outputs a detection result to the control unit 10. Note that the measurement device 2 is not necessarily required to include the gravity sensor 13.

The imaging unit 14 includes a vision sensor 14*a* and an imaging sensor 14*b*. The vision sensor 14*a* is a sensor called a dynamic vision sensor (DVS) or an event-based vision sensor (EVS). The vision sensor 14*a* captures an image of a predetermined imaging range through the lens 15.

The vision sensor 14*a* is an asynchronous image sensor in which a plurality of pixels having photoelectric conversion elements is two-dimensionally arranged and a detection circuit that detects an address event in real time is provided for every pixel. Note that an address event is an event that occurs for every address assigned to each of the plurality of pixels arranged two-dimensionally, and is, for example, a phenomenon in which a current value of a current based on charge generated in the photoelectric conversion element, or the amount of change thereof, exceeds a certain threshold value, or the like.

The vision sensor 14*a* detects the presence or absence of occurrence of an address event for every pixel, and in a case where occurrence of an address event is detected, a pixel signal is read as pixel data from the pixel in which the address event has occurred.

The vision sensor 14*a* performs a pixel-signal reading operation on a pixel in which occurrence of an address event has been detected, and hence can read at a much higher speed than a synchronous image sensor that performs a reading operation on each of all pixels at a predetermined frame rate. Further, the amount of data read in one frame is small.

Therefore, in the measurement system 1, movement of a target organism can be detected more quickly by using the vision sensor 14*a*. Furthermore, the vision sensor 14*a* can reduce the amount of data and also reduce power consumption.

The imaging sensor 14*b* is, for example, a charge coupled device (CCD) image sensor or a complementary metal-oxide-semiconductor (CMOS) image sensor, in which a plurality of pixels having photoelectric conversion elements is two-dimensionally arranged. The imaging sensor 14*b* captures images of a predetermined imaging range through the lens 15 at regular intervals in accordance with a frame rate, to generate image data. Note that, in the measurement device 2, a zone plate, a pinhole plate, or a transparent plate can be used instead of the lens 15.

Note that the vision sensor 14*a* and the imaging sensor 14*b* are arranged such that the sensors capture images of the substantially same imaging range through the lens 15. For example, it is only required to place a half mirror (not illustrated) between the vision sensor 14*a* and the imaging sensor 14*b*, and the lens 15 so that a part of light dispersed by the half mirror is incident on the vision sensor 14*a*, and the other part is incident on the imaging sensor 14*b*.

The stimulus generation device 3 is a device that generates (outputs) an external stimulus to an imaging range of which image is captured by the imaging unit 14, and gives an external stimulus to an organism present in the imaging range, and includes a light/heat generation device 30 and a stimulating-substance emission device 31.

The light/heat generation device 30 includes a lighting device 30*a* (light source) that applies light to an imaging range and a heat-source device 30*b* (heat source) that applies heat to the imaging range. The lighting device 30*a* is driven on the basis of control of the control unit 10, and can change the wavelength and intensity of light applied to the imaging range. The heat-source device 30*b* is driven on the basis of control of the control unit 10, and can change the temperature of the imaging range.

The stimulating-substance emission device 31 includes, for example, a container containing pheromone (stimulating substance, chemical substance) and having an opening/closing door, and can emit pheromone to an imaging range by opening and closing the opening/closing door on the basis of control of the control unit 10. Note that the lighting device 30*a* and the heat-source device 30*b* that are integrally provided as the light/heat generation device 30 may be provided separately.

Furthermore, light and temperature are common as external stimuli by which an organism exhibits chemotaxis, and hence, it is desirable that the stimulus generation device 3 includes at least the lighting device and the heat-source device 30*b* in consideration of general versatility. However, the stimulus generation device 3 may include only the stimulating-substance emission device 31 that emits a stimulating substance as an external stimulus. That is, the stimulus generation device 3 is only required to include at least one device that generates an external stimulus, and may omit any of the lighting device 30*a*, the heat-source device 30*b*, and the stimulating-substance emission device 31.

Furthermore, the stimulus generation device 3 may include a device that generates any of light, a temperature, and a stimulating substance, or a combination of two or more thereof as an external stimulus, specifically, any of the lighting device 30*a*, the heat-source device 30*b*, and the stimulating-substance emission device 31, or a combination of two or more thereof.

Furthermore, the stimulus generation device 3 may include a device that generates an external stimulus other than light, a temperature, and pheromone. For example, the stimulus generation device 3 may generate an external stimulus complying with a chemotaxis condition under which an organism exhibits chemotaxis, such as a pressure, a gravity, electricity, vibration, contact, and the like, for example.

2. Measurement Method as Embodiment

Next, an outline of a method for measuring a target organism as the embodiment will be described.

FIG. 2 is a view for explaining an example of measurement setting. FIG. 3 is a view for explaining an example of an operation time chart.

The control unit 10 performs measurement in accordance with measurement setting specified in advance as illustrated in FIG. 2. In the measurement setting, a measurement start condition, an operation time chart of the stimulus generation device 3, an identification program (identification method), and a measurement end condition are specified.

As the measurement start condition, a condition for starting measurement is specified, and for example, a time to start measurement, reception of a measurement start command input via the communication unit 12, or the like is specified.

As the operation time chart, a time chart according to which the stimulus generation device 3 is caused to generate an external stimulus complying with a chemotaxis condition that is a condition of external stimulus by which an organism exhibits chemotaxis, is specified. For example, according to the operation time chart illustrated in FIG. 3A, control is performed such that light is not applied from the lighting device 30*a*, heat is not output from the heat-source device 30*b*, and pheromone is not emitted from the stimulating-substance emission device 31 until five minutes elapse from start of measurement. Furthermore, for a duration from five-minute elapse to 10-minute elapse from start of the measurement, control is performed such that light having a wavelength of 420 nm and intensity of 3 W/m$^2$ is applied from the lighting device 30*a*, heat is not output from the heat-source device 30*b*, and pheromone is not emitted from the stimulating-substance emission device 31. Furthermore, for a duration from 10-minute elapse to 15-minute elapse from start of the measurement, control is performed such that light is not applied from the lighting device 30*a*, heat is not output from the heat-source device 30*b*, and pheromone is not emitted from the stimulating-substance emission device 31. Furthermore, for a duration from 15-minute elapse to 20-minute elapse from start of the measurement to elapse, control is performed such that light having a wavelength of 420 nm and intensity of 10 W/m$^2$ is applied from the lighting device 30*a*, heat is not output from the heat-source device 30*b*, and pheromone is not emitted from the stimulating-substance emission device 31.

Furthermore, according to the operation time chart illustrated in FIG. 3B, control is performed such that light is not applied from the lighting device 30*a*, heat is not output from the heat-source device 30*b*, and pheromone is not emitted from the stimulating-substance emission device 31 until one minute elapses from start of measurement. Furthermore, for a duration from one-minute elapse to 11-minute elapse from start of the measurement, control is performed such that light having a wavelength that is increased from 400 nm by 20 nm every minute is sequentially applied from the lighting device 30*a* at intensity of 5 W/m$^2$, heat is output from the heat-source device 30*b* so that a measurement range is at 15° C., and pheromone is not emitted from the stimulating-substance emission device 31. Furthermore, for a duration from 11-minute elapse to 21-minute elapse from start of the measurement, control is performed such that light having a wavelength that is increased from 400 nm by 20 nm every minute is sequentially applied from the lighting device 30*a* at intensity of 5 W/m$^2$, heat is output from the heat-source device 30*b* so that a measurement range is at 20° C., and pheromone is not emitted from the stimulating-substance emission device 31. Furthermore, for a duration from 21-minute elapse to 31-minute elapse from start of the measurement, control is performed such that light having a wavelength that is increased from 400 nm by 20 nm every minute is sequentially applied from the lighting device 30*a* at intensity of 5 W/m$^2$, heat is output from the heat-source device 30*b* so that a measurement range is at 25° C., and pheromone is not emitted from the stimulating-substance emission device 31.

As described above, in the operation time chart, what kind of external stimulus is to be generated from the stimulus generation device 3 and what time such external stimulus is to be generated, for a measurement range, are specified.

In the identification program, a program (method) for identifying a target organism is designated, and for example, identification by machine learning, rule-based identification, identification by input/output parameters, and the like are specified.

As the measurement end condition, a condition for ending measurement is specified, and for example, a time to end measurement, reception of a measurement end command input via the communication unit 12, or the like is specified.

Figure 4:
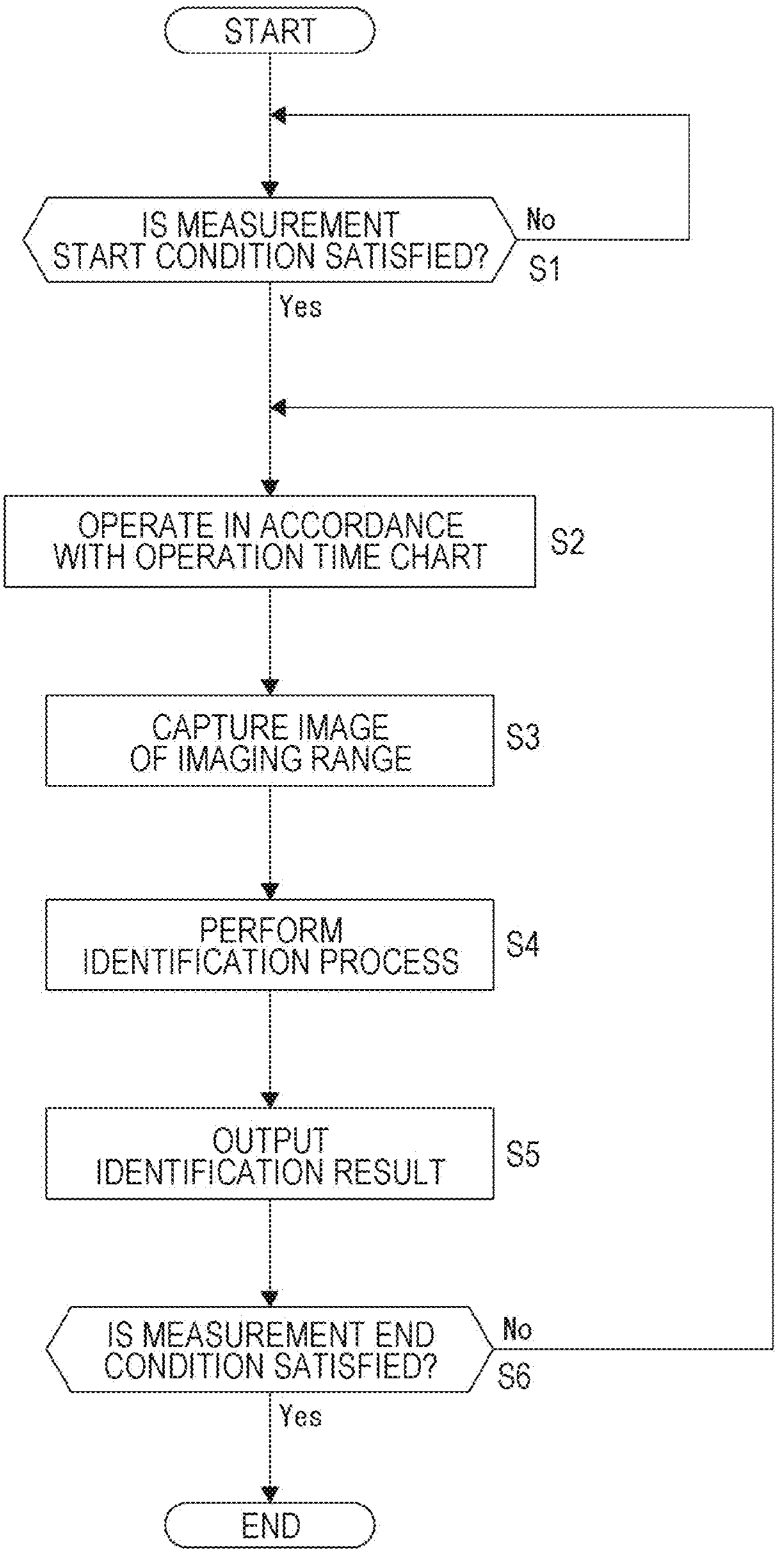
FIG. 4 is a flowchart illustrating a process procedure of a measurement method.

FIG. 4 is a flowchart illustrating a process procedure of the measurement method. As illustrated in FIG. 4, in a step S1, the control unit 10 determines whether or not the measurement start condition specified in the measurement setting is satisfied. Then, the control unit 10 repeats the step S1 until the measurement start condition is satisfied.

On the other hand, in a case where the measurement start condition is satisfied (Yes in the step S1), the stimulus control unit 21 causes the stimulus generation device 3 to operate so as to generate an external stimulus complying with the chemotaxis condition of an organism according to the operation time chart specified in the measurement setting, in a step S2. In a step S3, the imaging control unit 22 controls the imaging unit 14 such that an image of an imaging range is captured, to acquire pixel data and image data. Thereafter, in a step S4, the class identification unit 23 performs an identification process.

In the identification process, the class identification unit 23 performs measurement on a target organism on the basis of the image (pixel data and image data) captured by the imaging unit 14. In the present embodiment, the class identification unit 23 derives identification information from the image captured by the imaging unit 14 for every condition for an external stimulus and compares the identification information with definition information stored in the memory 11, to detect the target organism. Furthermore, the class identification unit 23 derives an identification result such as the number, the density, and the average activity level of the detected target organism.

Figure 6:
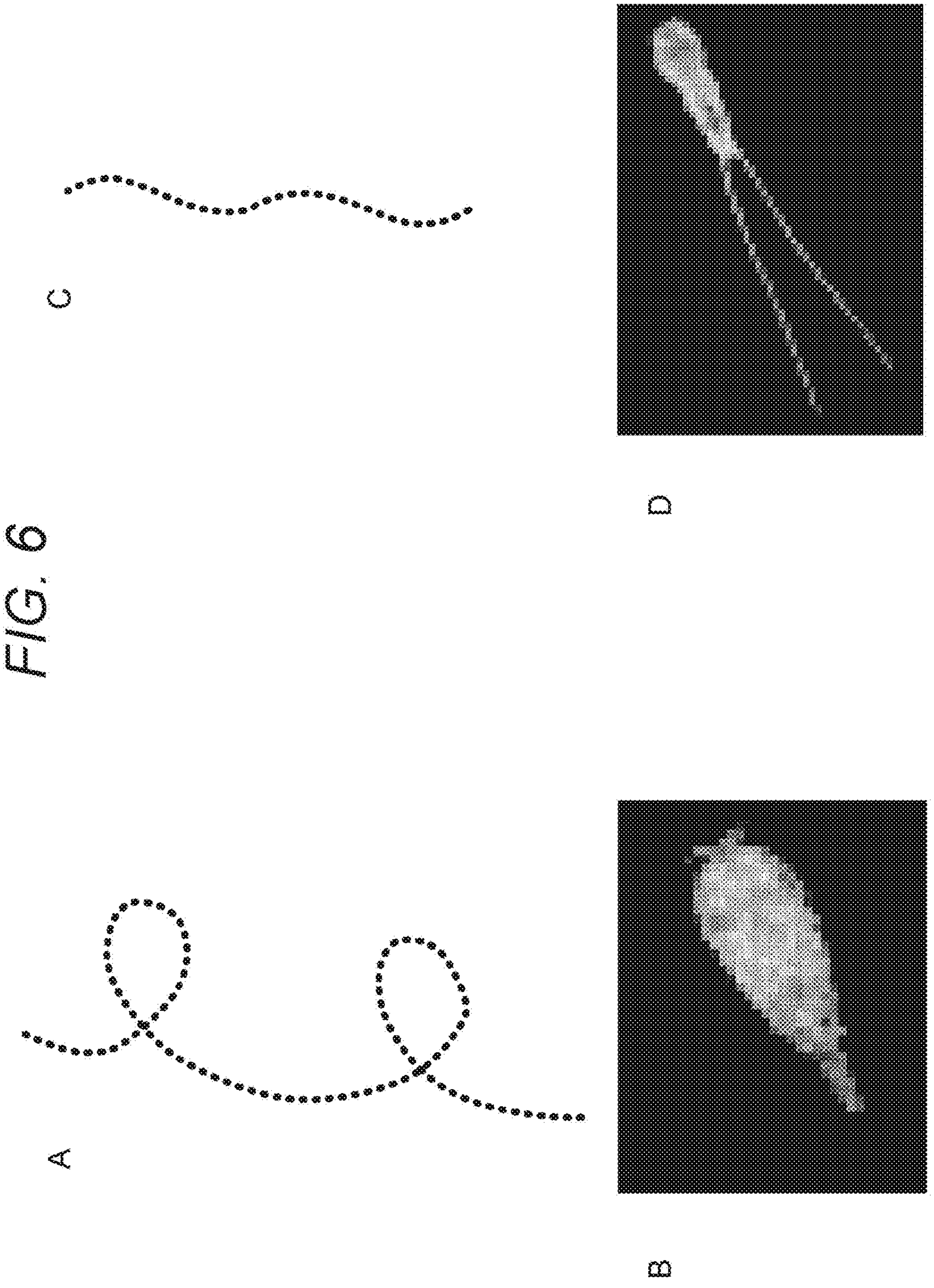
FIG. 6 is a view for explaining examples of a trajectory and an image of a detected object.

FIG. 5 is a view for explaining the definition information about the target organism. FIG. 6 is a view for explaining examples of a trajectory and an image of a detected object. FIG. 7 is a view for explaining an example of the identification result.

The definition information as illustrated in FIG. 5 is provided for every target organism and stored in the memory 11. The definition information includes the type (biological name) of the target organism, external stimulus information, chemotactic response information, and image information. The external stimulus information indicates a condition for an external stimulus by which the target organism exhibits chemotaxis.

The chemotactic response information is information detected mainly on the basis of an image captured by the vision sensor 14*a,* and is information based on a behavior performed by the target organism in exhibiting chemotaxis in response to an external stimulus. The chemotactic response information is, for example, information such as a direction of movement (positive or negative) with respect to a source of an external stimulus, a speed, and a trajectory. Note that the chemotactic response information may be information detected on the basis of an image captured by the imaging sensor 14*b*. The chemotactic response information illustrated in FIG. 5 is merely an example, and a part of the information may be omitted, or other information may be included.

The image information is information detected mainly on the basis of an image captured by the imaging sensor 14*b,* and is information about an outer shape of the target organism. The image information is, for example, information such as the size of the target organism and the presence or absence of a tactile organ. Note that the image information may be information detected on the basis of an image captured by the vision sensor 14*a*. The image information illustrated in FIG. 5 is merely an example, and a part of the information may be omitted, or other information may be included.

These pieces of definition information are stored in the memory 11 by respective different methods for identification programs. For example, in a rule-based identification program, the definition information is set in advance by a user and stored in the memory 11. Furthermore, in an identification program by machine learning, the definition information is generated and updated by machine learning in a learning mode and stored in the memory 11.

Furthermore, the definition information may include the direction of gravity detected by the gravity sensor 13 and external environment information acquired via the communication unit 12. Note that, as the external environment information, electric conductivity, a temperature, ph, a concentration of gas (methane, hydrogen, helium, for example), a concentration of metal (manganese, iron, for example), and the like can be considered.

The class identification unit 23 detects an object present in an imaging range on the basis of an image (pixel data) captured by the vision sensor 14*a*. For example, the class identification unit 23 creates one frame data on the basis of pixel data input within a predetermined period, and detects a pixel group within a predetermined range in which motion has been detected in the frame data, as an object.

Furthermore, the class identification unit 23 follows an object between a plurality of pieces of frame data by pattern matching or the like as illustrated in FIGS. 6A and 6C. Then, the class identification unit 23 derives a direction of movement with respect to a stimulus source, a speed, and a trajectory, as identification information, on the basis of the result of following the object. In FIGS. 6A and 6C, the position of an object for every piece of frame data is indicated by a black circle. In the example of FIG. 6A, the object moves in a spiral manner, and in the example of FIG. 6C, the object moves in a serpentine manner.

Note that a period at which the class identification unit 23 creates frame data from pixel data may be the same as or shorter than a period (frame rate) at which the imaging sensor 14*b* acquires image data.

Furthermore, the class identification unit 23 extracts an image portion corresponding to the object from the image data input from the imaging sensor 14*b* for the object from which the identification information has been derived, as illustrated in FIGS. 6B and 6D. Note that FIG. 6B illustrates an image of an object following the trajectory illustrated in FIG. 6A, and FIG. 6D is an image of an object following the trajectory illustrated in FIG. 6C.

Then, the class identification unit 23 derives the size of the object, the presence or absence of a tactile organ, and the like as the identification information by image analysis on the basis of the extracted image portion. Note that a known method can be used for the image analysis, and hence description thereof is omitted here.

The class identification unit 23 collates the external stimulus generated by the stimulus generation device 3 and the identification information (the direction of movement, the trajectory, the speed, the size, the presence or absence of a tactile organ) derived for the detected object with the definition information conforming to a designated identification program, to determine whether or not the object is any target organism. Here, for example, if the derived identification information about the object falls within a range indicated by the definition information about the target organism, the class identification unit 23 determines that the derived object is a type indicated by the definition information.

Then, as illustrated in FIG. 7, the class identification unit 23 derives the number of target organisms (for every type) by counting the detected target organisms of every type. Furthermore, the class identification unit 23 derives the density and the average activity level of target organisms of every type. Note that the density is derived on the basis of the number of target organisms in the imaging range, and the average activity level is derived on the basis of the speed of the target organisms. Note that, as illustrated in FIG. 7, for objects other than the target organism, the number, the density, and the average activity level are derived for every similar characteristic, under the names, “unknown A” and “unknown B”, for example.

Thereafter, in a step S5 (see FIG. 4), the class identification unit 23 outputs the identification result indicating the type, the number, the density, and the average activity level of the detected target organisms and an image captured by the imaging sensor 14*b* by storing them into the memory 11, transmitting them to an external device via the communication unit 12, and the like.

In a step S6, the control unit 10 determines whether or not the measurement end condition specified in the measurement setting is satisfied. Then, the control unit 10 repeats the steps S2 to S5 until the measurement end condition is satisfied. In a case where the measurement end condition is satisfied (Yes in the step S6), the control unit 10 stops the stimulus generation device 3 and ends the image capture in the imaging unit 14, to end the process.

3. Use Examples

Hereinafter, use examples of the measurement system 1 will be described. Note that, in first to fourth use examples described below, light is generated from the lighting device 30*a* as an external stimulus, and no external stimulus (heat, pheromone) is generated from the heat-source device 30*b* and the stimulating-substance emission device 31. Hence, description of control of the heat-source device 30*b* and the stimulating-substance emission device 31 is omitted.

[3-1. First Use Example]

Figure 8:
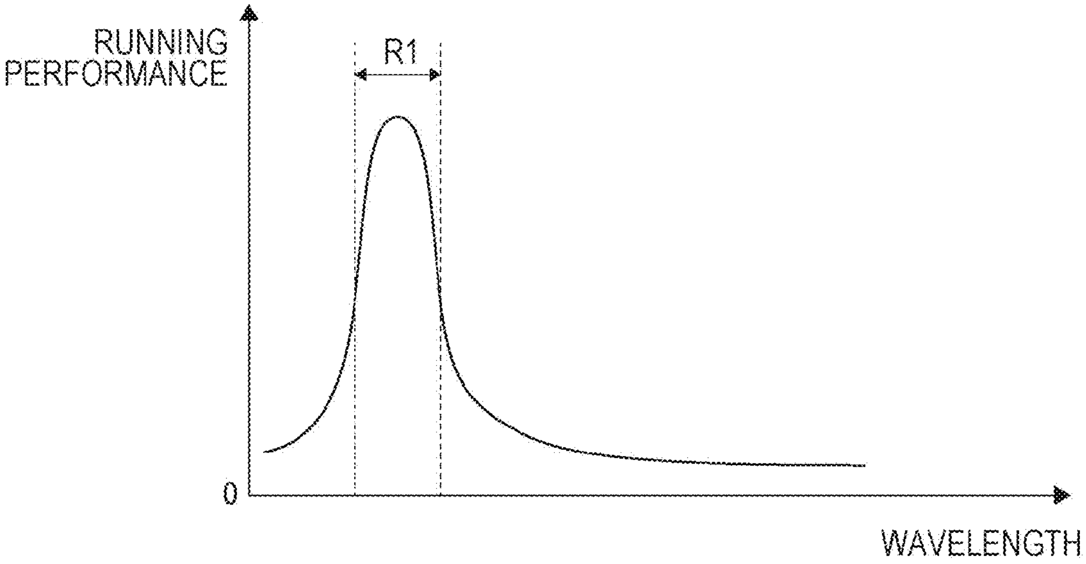
FIG. 8 is a view for explaining a wavelength of applied light in a first use example.

FIG. 8 is a view for explaining a wavelength of applied light in the first use example. In the first use example, an external stimulus by which a target organism exhibits positive chemotaxis is generated from the stimulus generation device 3.

For example, it is assumed that the target organism shows a relationship between running performance and a wavelength as illustrated in FIG. 8. In such a case, the target organism exhibits positive running performance in a wavelength range R1, and thus the measurement setting is specified such that light in the wavelength range R1 by which the target organism exhibits positive running performance is applied to an imaging range from the lighting device 30*a*. Then, the stimulus control unit 21 causes the lighting device 30*a* to apply light in the wavelength range R1 by which the target organism exhibits positive running performance, to the imaging range, according to the measurement setting.

The imaging control unit 22 causes the vision sensor 14*a* to acquire pixel data and causes the imaging sensor 14*b* to acquire image data while the stimulus generation device 3 is applying light by which the target organism exhibits positive running performance.

The class identification unit 23 derives an identification result of the target organism on the basis of the pixel data and the image data acquired by the imaging unit 14.

In the first use example, light by which the target organism exhibits positive running performance is applied to the imaging range, so that the target organism present in the imaging range moves toward the light source. Furthermore, in the first use example, the target organism present outside the imaging range moves to the light source, and thus moves to the imaging range. Therefore, in the first use example, the presence or absence of the target organism can be efficiently determined.

[3-2. Second Use Example]

Figure 9:
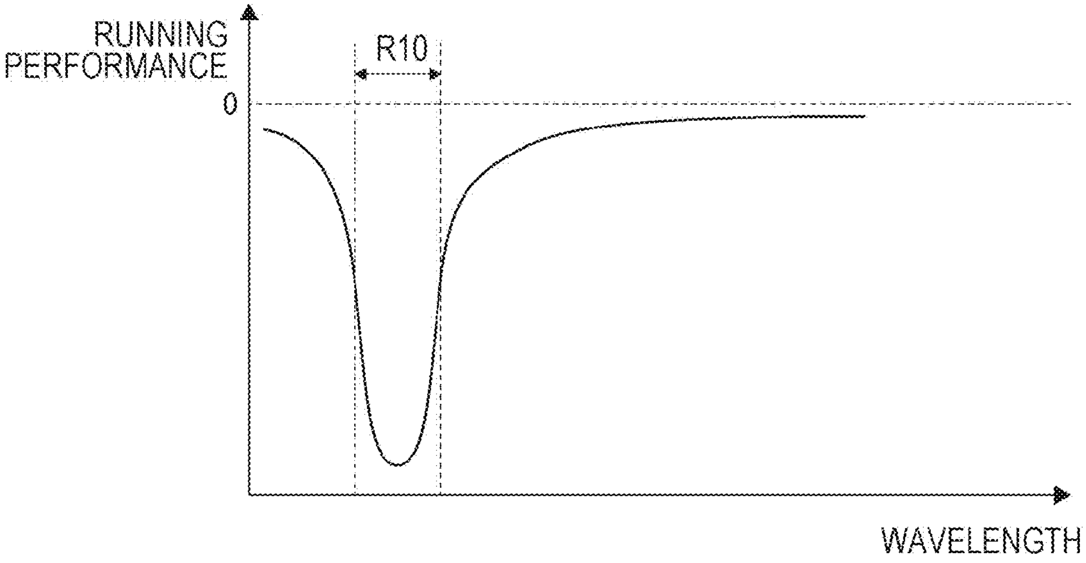
FIG. 9 is a view for explaining a wavelength of applied light in a second use example.

FIG. 9 is a view for explaining a wavelength of applied light in the second use example. In the second use example, unlike in the first use example, an external stimulus by which an organism other than the target organism (, which will be hereinafter referred to as a non-target organism) exhibits negative chemotaxis is generated from the stimulus generation device 3. Note that, in the second use example, it is desirable that an external stimulus by which the non-target organism exhibits negative chemotaxis and the target organism does not exhibit negative chemotaxis is generated from the stimulus generation device 3. However, an external stimulus by which the target organism exhibits negative chemotaxis may be generated so long as the external stimulus causes exhibition of relatively weak negative chemotaxis such as a lower speed associated with chemotaxis as compared to that of the non-target organism.

For example, it is assumed that the non-target organism shows a relationship between running performance and a wavelength as illustrated in FIG. 9. In such a case, the non-target organism exhibits negative running performance in a wavelength range R10, and thus the measurement setting is specified such that light in the wavelength range R10 by which the non-target organism exhibits negative running performance is applied to the imaging range from the lighting device 30*a*. Then, the stimulus control unit 21 causes the lighting device 30*a* to apply light in the wavelength range R10 by which the non-target organism exhibits negative running performance, to the imaging range, according to the measurement setting.

The imaging control unit 22 causes the vision sensor 14*a* to acquire pixel data and causes the imaging sensor 14*b* to acquire image data while the stimulus generation device 3 is applying light by which the non-target organism exhibits negative running performance.

The class identification unit 23 derives an identification result of the target organism on the basis of the pixel data and the image data acquired by the imaging unit 14.

In the second use example, light by which the non-target organism exhibits negative running performance is applied to the imaging range, so that the non-target organism present in the imaging range moves in a direction away from the light source, in other words, moves to outside the imaging range. Therefore, in the second use example, the non-target organism is excluded from the imaging range, and efficient measurement limited to the target organism can be performed.

[3-3. Third Use Example]

Figure 10:
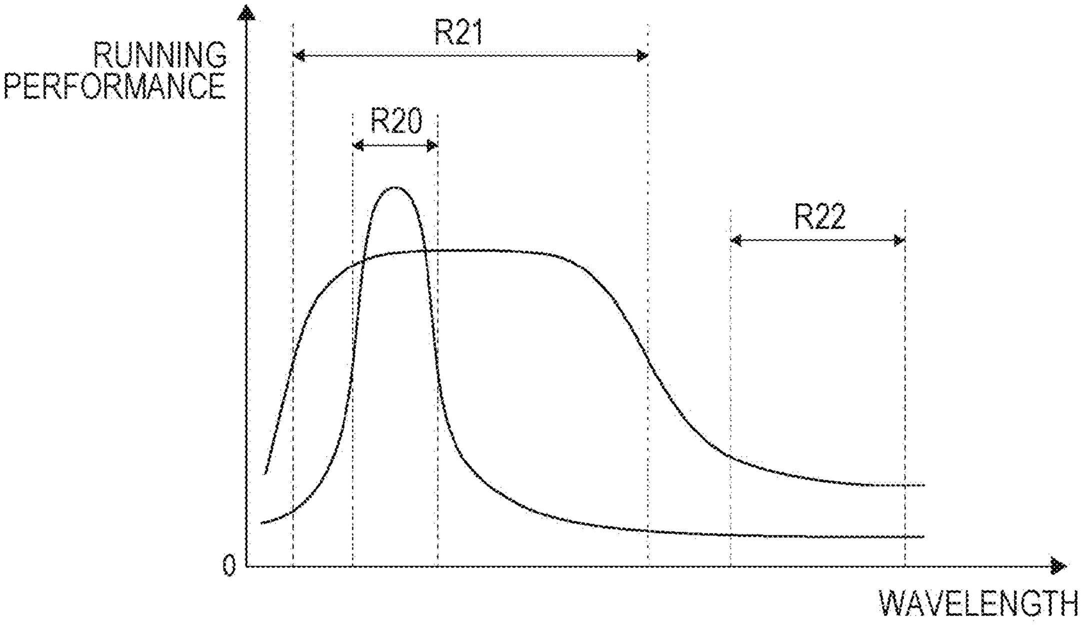
FIG. 10 is a view for explaining a wavelength of applied light in a third use example.

FIG. 10 is a view for explaining a wavelength of applied light in the third use example. In the third use example, unlike in the first use example and the second use example, an external stimulus by which at least the target organism does not exhibit chemotaxis (positive chemotaxis and negative chemotaxis) is generated from the stimulus generation device 3. Note that the external stimulus that does not cause exhibition of chemotaxis includes not only an external stimulus that does not cause exhibition of chemotaxis at all, but also an external stimulus that causes exhibition of chemotaxis at a lower rate than other external stimuli.

For example, it is assumed that two target organisms show relationships between a running performance and a wavelength as illustrated in FIG. 10. In such a case, one of the target organisms exhibits running performance in response to light in a wavelength range R20, and the other of the target organisms exhibits running performance in response to light in a wavelength range R21. Thus, the measurement setting is specified such that light in a wavelength range R22 by which either of the target organisms does not exhibit running performance is applied to the imaging range from the lighting device 30*a*. Then, the stimulus control unit 21 causes the lighting device 30*a* to apply light in the wavelength range R22 by which either of the target organisms does not exhibit running performance, to the imaging range, according to the measurement setting.

The imaging control unit 22 causes the vision sensor 14*a* to acquire pixel data and causes the imaging sensor 14*b* to acquire image data while the stimulus generation device 3 is applying light by which either of the target organisms does not exhibit running performance.

The class identification unit 23 derives an identification result of the target organism on the basis of the pixel data and the image data acquired by the imaging unit 14.

Here, in the case of measuring a target organism in a place where natural light does not reach, such as at night or in deep water, it is necessary to apply illumination light to the imaging range. At that time, if illumination light by which the target organism exhibits chemotaxis is applied to the imaging range, the target organism in the imaging range cannot be accurately measured. Specifically, to apply illumination light by which the target organism exhibits positive running performance to the imaging range would increase the number of target organisms in the imaging range. Furthermore, to apply illumination light by which the target organism exhibits negative running performance to the imaging range would reduce the number of target organisms in the imaging range.

Then, in the third use example, illumination light by which the target organism does not exhibit chemotaxis is applied to the imaging range, and thus it is possible to capture an image without affecting the target organism, which enables efficient measurement in an original natural environment.

[3-4. Fourth Use Example]

Figure 11:
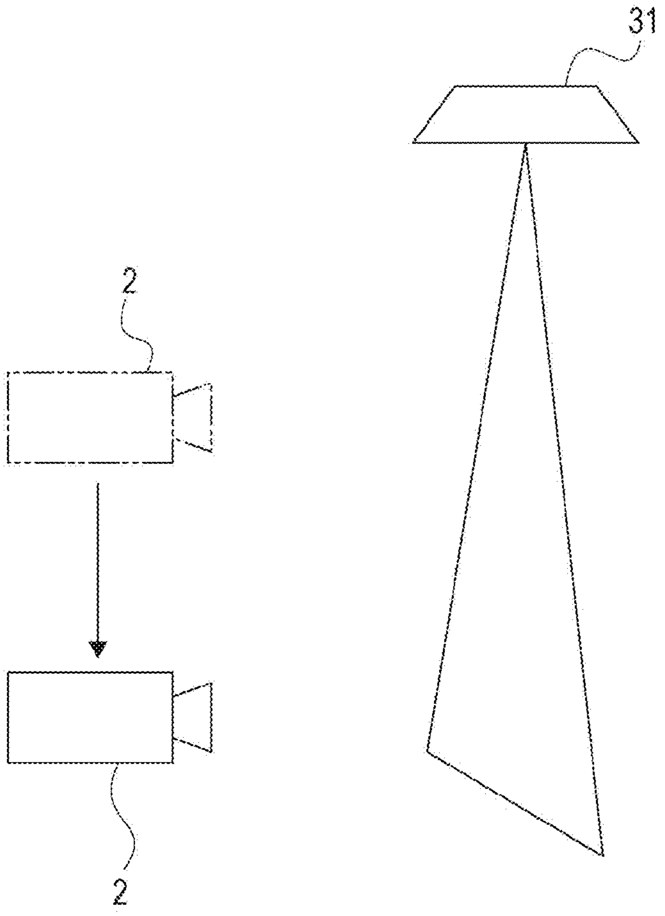
FIG. 11 is a view for explaining measurement in a fourth use example.

FIG. 11 is a view for explaining measurement in a fourth use example. In the fourth use example, the measurement device 2 captures an image while moving in the third use example. Thus, the lighting device 30*a* applies light in the wavelength range R22 by which either of the target organisms does not exhibit running performance, to the imaging range, in the manner similar to that in the third use example.

Then, as illustrated in FIG. 11, the measurement device 2 moves along the optical axis direction of the light applied from the light/heat generation device 30 of the stimulus generation device 3, for example. Note that the measurement device 2 may be connected to a moving mechanism (not illustrated) and controlled such that it moves under the control of the control unit 10, or may be moved manually. Furthermore, the measurement device 2 is only required to be capable of moving along a predetermined direction. For example, the measurement device 2 may move along the direction of gravity or may move along a direction orthogonal to the optical axis of light applied from the light/heat generation device 30.

Then, the imaging control unit 22 causes the vision sensor 14*a* to acquire pixel data and causes the imaging sensor 14*b* to acquire image data while the measurement device 2 is moving along the optical axis direction.

The class identification unit 23 derives an identification result of the target organism on the basis of the pixel data and the image data acquired by the imaging unit 14.

In the fourth use example, the imaging range is moved, which enables measurement of target organisms in a wide range. Furthermore, in the fourth use example, for example, in a case where the optical axis direction and the direction of gravity coincide with each other and the measurement device 2 is moved in the direction of gravity, a distribution of target organisms in the direction of gravity can be measured.

4. Specific Examples

The measurement system 1 is intended to be used underwater and on land. For example, in water, the measurement system 1 is intended to be used for measurement performed on organisms used for feed (rotifer, brine shrimp, copepod), parasites parasitic on cultivated animals (fish louse, parasitic copepod, parasitic ciliate, Benedenia seriolae), larvae of deep-sea animals, zooplankton indigenous to hydrothermal plume, phytoplankton causing red tide, and fish, as target organisms. Furthermore, on land, the measurement system 1 is intended to be used for measurement performed on harmful insects such as a mosquito, a moth, or a fly, as target organisms. Below, description will be given by way of specific examples.

[4-1. First Specific Example]

Figure 12:
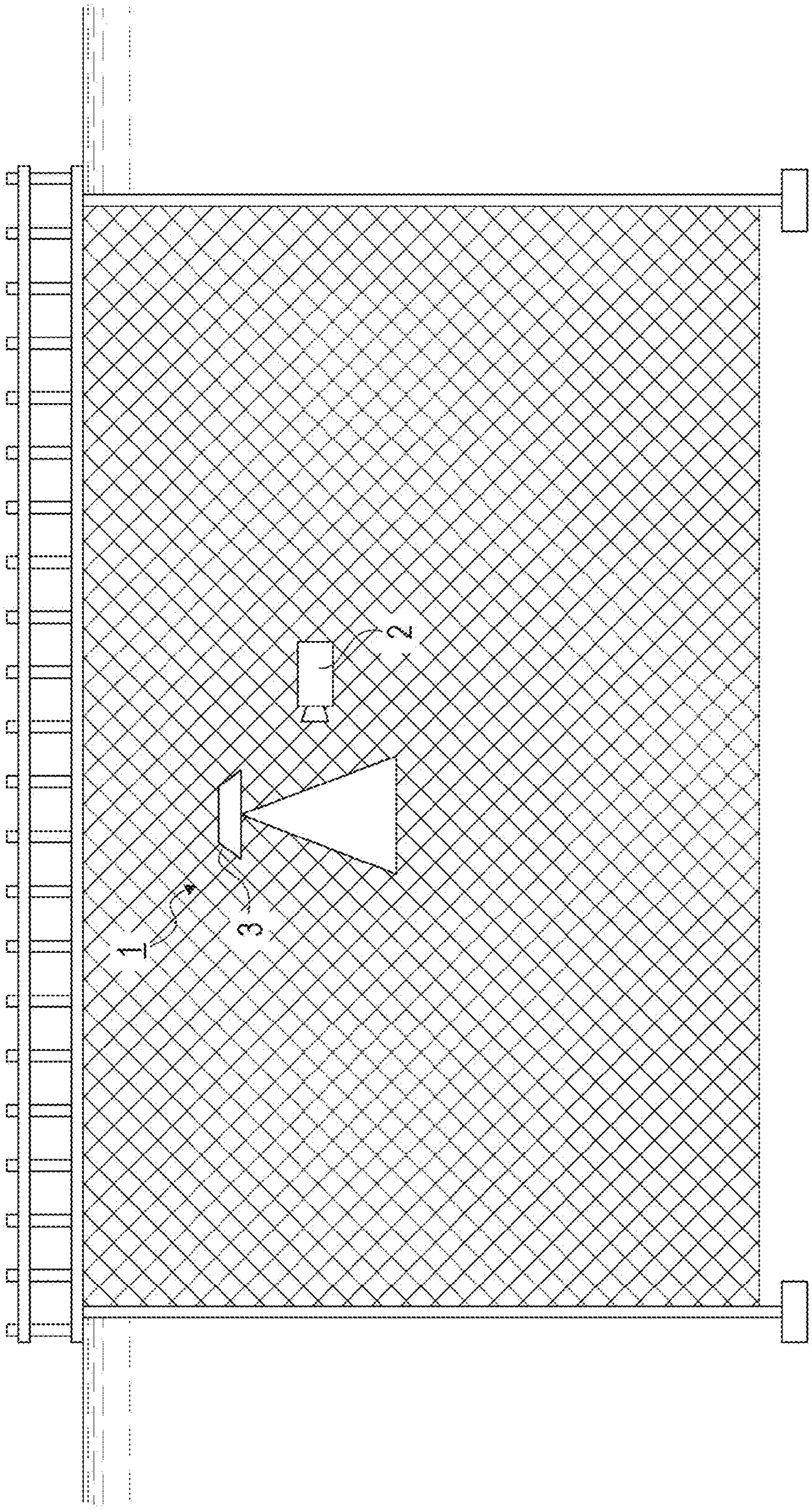
FIG. 12 is a view for explaining an example in which the measurement system is used in an aquaculture farm.

FIG. 12 is a view for explaining an example in which the measurement system 1 is used in an aquaculture farm. In a first specific example, as illustrated in FIG. 12, the measurement system 1 is placed in an aquaculture farm, and estimates the amount of larvae of brine shrimps used for feed in fish culture. Furthermore, in the first specific example, it is assumed that machine learning is designated as the identification program.

In this case, the class identification unit 23 estimates the number of brine shrimps (the amount of larvae) by machine learning in an environment in the aquaculture farm where suspended matters such as zooplankton and dust coexist.

Here, a brine shrimp is known as exhibiting remarkable running performance in response to light having a wavelength of around 420 nm. Furthermore, copepods that account for most, 80% or more on average, of zooplankton community are known as exhibiting remarkable running performance in response to light having a wavelength of around 400 to 500 nm.

Thus, in a learning mode, the stimulus control unit 21 causes the lighting device 30*a* to apply light having a wavelength of 420 nm and light having a wavelength of 530 nm to each of liquid samples, each containing only one of brine shrimps, copepods, and dust. The imaging control unit 22 causes the imaging unit 14 to operate and capture an image while the stimulus generation device 3 is applying light of each wavelength.

The class identification unit 23 learns identification information about the brine shrimps, the copepods, and the dust as training data on the basis of the image captured by the imaging unit 14.

Thus, in the learning mode, definition information about the brine shrimps, the copepods, and the dust is generated on the basis of the respective pieces of identification information about the brine shrimps, the copepods, and the dust in a case where light having a wavelength of 420 nm is applied, and respective pieces of the identification information about the brine shrimps, the copepods, and the dust in a case where light having a wavelength of 530 nm is applied.

Then, in the aquaculture farm where the brine shrimps, the zooplankton, and the dust coexist, the stimulus control unit 21 causes the lighting device 30*a* to apply light having a wavelength of 420 nm and light having a wavelength of 530 nm. The imaging control unit 22 causes the imaging unit 14 to operate and capture an image while the stimulus generation device 3 is applying light of each wavelength.

The class identification unit 23 derives the amount of larvae of the brine shrimps (identification result) using the definition information learned in the learning mode on the basis of the image captured by the imaging unit 14.

As described above, the measurement system 1 can efficiently and accurately derive the identification result of the target organism in the unknown liquid sample by learning the characteristic of the target organism in advance by machine learning.

[4-2. Second Specific Example]

In a second specific example, the number of larval fish that mostly inhabit shallow sea areas is estimated. Furthermore, in the second specific example, it is assumed that rule base is designated as the identification program.

Here, it is assumed that larval fish to be measured has green visual sensitivity characteristic and has blue visual sensitivity characteristic when becoming an adult fish. That is, the larval fish to be measured exhibits running performance in response to light having a wavelength of around 550 nm (green light).

In this case, the stimulus control unit 21 causes the lighting device 30*a* to apply light having a wavelength of 550 nm. The imaging control unit 22 causes the imaging unit 14 to operate and capture an image while the stimulus generation device 3 is applying light. The class identification unit 23 derives an identification result of the larval fish using the definition information stored in the memory 11 in accordance with the rule base on the basis of the image captured by the imaging unit 14.

[4-3. Third Specific Example]

In a third specific example, the number of nematodes existing in soil is estimated. Furthermore, in the third specific example, it is assumed that rule base is designated as the identification program.

Here, a nematode to be measured is known as exhibiting thermotaxis in which it moves to a temperature field at around 25° C.

The stimulus control unit 21 causes the heat-source device 30*b* to operate so that a measurement range is at 25° C. The imaging control unit 22 causes the imaging unit 14 to operate and capture an image while the temperature is under the control of the heat-source device 30*b*.

The class identification unit 23 derives an identification result of the nematodes using the definition information stored in the memory 11 in accordance with the rule base on the basis of the image captured by the imaging unit 14.

5. Another Example of Configuration of Measurement System

Note that the embodiment is not limited to the specific examples described above, and can adopt various configurations as modifications.

In the embodiment described above, the measurement system 1 includes one measurement device 2 and one stimulus generation device 3. However, the number of the measurement devices 2 or the stimulus generation devices 3 is not limited to one, and a plurality of measurement devices 2 or a plurality of stimulus generation devices 3 may be provided.

Figure 13:
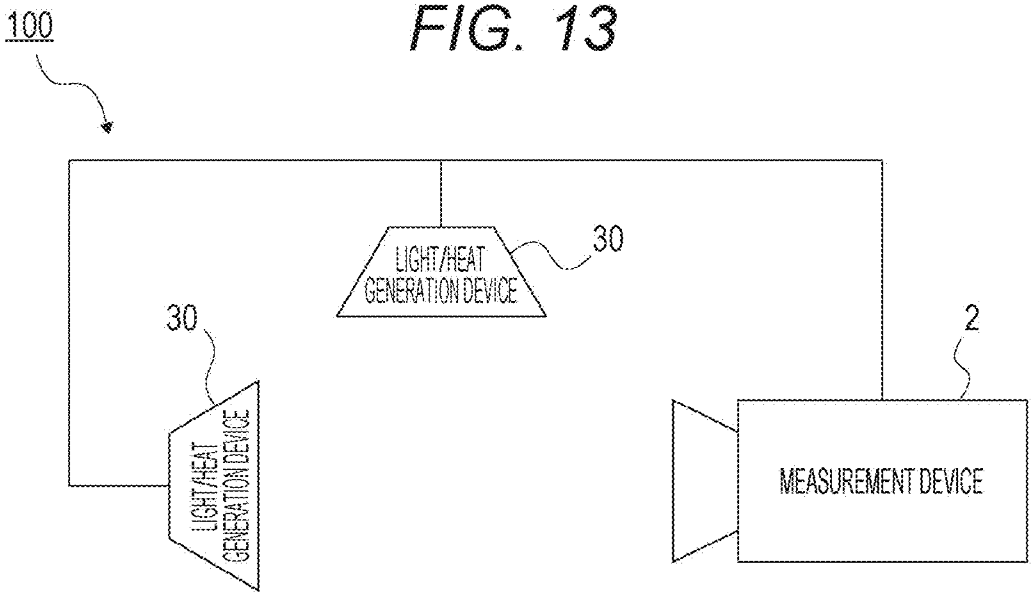
FIG. 13 is a view for explaining a configuration of a measurement system according to a modification.

FIG. 13 is a view for explaining a configuration of a measurement system 100 according to a modification. As illustrated in FIG. 13, the measurement system 100 of the modification includes one measurement device 2 and two stimulus generation devices 3 (light/heat generation devices 30). The two light/heat generation devices 30 are arranged so as to be capable of applying light in directions orthogonal to each other, and can apply light having wavelengths different from each other to the imaging range.

In the measurement system 100 described above, light of different wavelengths can be applied from the two light/heat generation devices 30, and thus identification information about a target organism exhibiting running performance in response to light of different wavelengths can be derived by one-time measurement, which enables efficient measurement.

Figure 14:
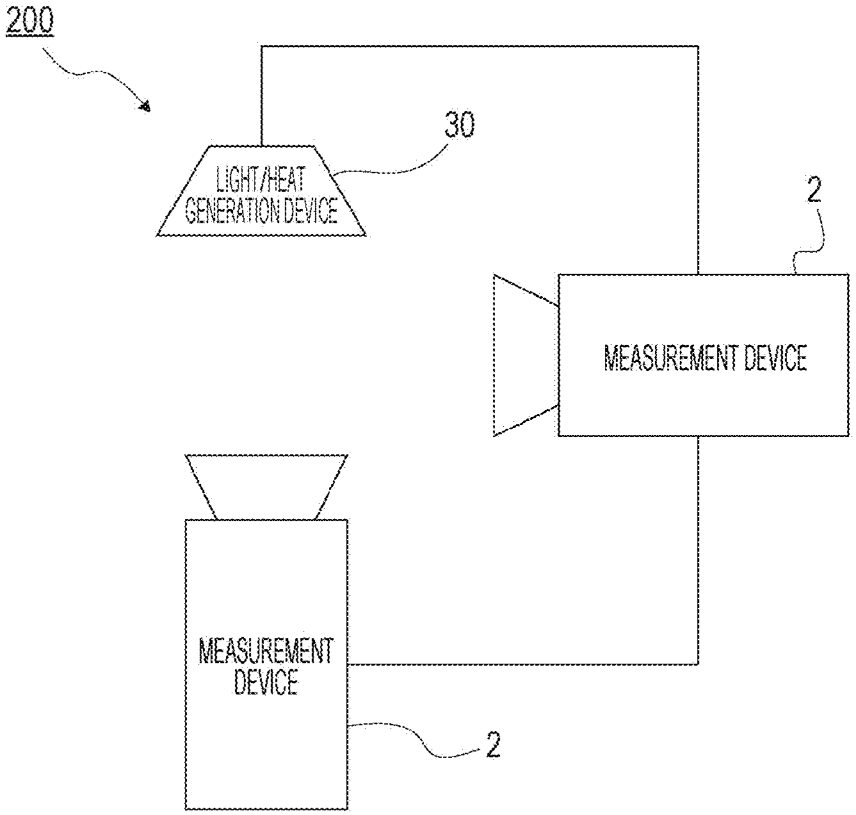
FIG. 14 is a view for explaining a configuration of a measurement system according to another modification.

FIG. 14 is a view for explaining a configuration of a measurement system 200 according to another modification. As illustrated in FIG. 14, the measurement system 200 of the modification includes two measurement devices 2 and one stimulus generation device 3 (light/heat generation device 30). The two measurement devices 2 are arranged so as to be capable of capturing images in directions orthogonal to each other.

In the measurement system 100 described above, images can be captured by the two measurement devices 2 (imaging units 14), and thus three-dimensional movement of an object can be detected, which enables more efficient measurement.

Note that, in a case where two measurement devices 2 are provided, one of the measurement devices 2 may include only the imaging unit 14.

Furthermore, in the embodiment described above, the imaging unit 14 includes the vision sensor 14*a* and the imaging sensor 14*b*. However, the imaging unit 14 may include either the vision sensor 14*a* or the imaging sensor 14*b* so long as an image from which identification information indicating at least chemotaxis can be derived can be captured. Furthermore, the imaging unit 14 may include a single photon avalanche diode (SPAD) sensor instead of the vision sensor 14*a* and the imaging sensor 14*b*.

Furthermore, in the embodiment described above, identification information is derived on the basis of pixel data acquired by the vision sensor 14*a* and image data acquired by the imaging sensor 14*b*. However, identification information may be derived on the basis of one or both of pixel data acquired by the vision sensor 14*a* and image data acquired by the imaging sensor 14*b*. Furthermore, control may be performed such that only the vision sensor 14*a* is driven with the imaging sensor 14*b* kept stopped, and the vision sensor 14*a* and the imaging sensor 14*b* are driven when the vision sensor 14*a* acquires pixel data.

Furthermore, in the embodiment described above, the lighting device 30*a* can change the wavelength and intensity of applied light. However, the lighting device 30*a* may be configured so as to be capable of selecting the presence or absence of blinking, changing the frequency of blinking, selecting the presence or absence of polarized light, changing the direction of polarized light, changing the size of the light source, changing the shape of the light source, changing the orientation of the light source with respect to the direction of gravity and the direction of the measurement device 2, the direction of propagation, or the like, in addition to, or instead of, changing the wavelength and intensity of applied light, in accordance with the chemotaxis of an organism.

6. Conclusion of Embodiment

As described above, the measurement device 2 of the embodiment includes the stimulus control unit 21 configured to cause the stimulus generation device 3 to generate an external stimulus complying with a chemotaxis condition of an organism, the imaging unit 14 configured to capture an image of a predetermined imaging range in which the external stimulus is generated, and a measurement unit (class identification unit 23) configured to measure a target organism on the basis of the image captured by the imaging unit 14.

With the configuration described above, it is possible to perform measurement on the target organism using the chemotaxis of the organism.

Therefore, the measurement device 2 can efficiently measure plants/animals as target organisms using the chemotaxis of the organism.

In the measurement device 2 according to the present technology described above, the imaging unit 14 includes the vision sensor 14*a* configured to asynchronously acquire pixel data in accordance with the amount of light incident on each of a plurality of pixels two-dimensionally arranged.

This makes it possible to read only pixel data of a pixel in which an event has occurred and measure the target organism on the basis of the pixel data.

Therefore, the measurement device 2 can reduce power consumption.

In the measurement device 2 according to the present technology described above, the stimulus control unit 21 generates an external stimulus by which the target organism exhibits positive chemotaxis.

This makes it possible to gather the target organism in the imaging range.

Therefore, the measurement device 2 can efficiently measure the presence or absence of the target organism.

In the measurement device 2 according to the present technology described above, the stimulus control unit 21 causes generation of an external stimulus by which a non-target organism other than the target organism exhibits negative chemotaxis.

This makes it possible to exclude the non-target organism from the imaging range.

Therefore, the measurement device 2 can exclude the non-target organism and perform measurement limited to the target organism.

In the measurement device 2 according to the present technology described above, the stimulus control unit 21 causes generation of an external stimulus by which a non-target organism other than the target organism exhibits negative chemotaxis and the target organism does not exhibit negative chemotaxis.

This makes it possible to reduce exclusion of the target organism from a target range while excluding the non-target organism from the imaging range.

Therefore, the measurement device 2 can accurately measure the target organism.

In the measurement device 2 according to the present technology described above, the stimulus control unit 21 causes generation of an external stimulus by which the target organism does not exhibit chemotaxis.

This makes it possible to capture an image without being affected by the external stimulus. Therefore, the measurement device 2 can accurately measure the target organism without being affected by the external stimulus.

In the measurement device 2 according to the present technology described above, the external stimulus is light and the stimulus control unit 21 causes application of light by which the target organism does not exhibit chemotaxis.

This makes it possible to measure the target organism in a state where it does not exhibit running performance even in a dark external environment.

Therefore, the measurement device 2 can accurately measure the target organism without being affected by the external stimulus.

In the measurement device 2 according to the present technology described above, the imaging unit 14 captures an image while being moved along a predetermined direction.

This enables wide-range measurement.

Therefore, the measurement device 2 can measure the target organism in a wider range.

In the measurement device 2 according to the present technology described above, the measurement unit (class identification unit 23) derives information (identification information) based on a behavior performed by the target organism in exhibiting chemotaxis on the basis of the image captured by the imaging unit 14, to specify the target organism on the basis of the information.

This makes it possible to measure an organism that exhibits chemotaxis.

Therefore, the measurement device 2 can more accurately specify the target organism using the information based on a behavior performed in exhibiting chemotaxis.

In the measurement device 2 according to the present technology described above, the measurement unit (class identification unit 23) derives at least one of the number, the density, or the average activity level of target organism.

This makes it possible to measure the actual status of the target organism.

Therefore, the measurement device 2 can specify at least one of the number, the density, or the average activity level of target organism.

In the measurement device 2 according to the present technology described above, the imaging unit 14 includes the vision sensor **14*a* and the imaging sensor 14*b*** that captures images at regular intervals in accordance with a frame rate.

This makes it possible to measure the target organism using one or both of the images captured by the vision sensor **14*a* and the imaging sensor 14*b***.

Furthermore, the measurement device 2 uses information based on the image captured by the vision sensor **14*a*, and thus the image captured by the imaging sensor 14*b*** may be coarse as compared with that in a case where the target organism is measured using only the imaging sensor. This makes it possible to capture an image in a wider range than that in a case where only the imaging sensor is used, with the same number of pixels.

In the measurement device 2 according to the present technology described above, the stimulus control unit 21 causes the stimulus generation device 3 to apply light having a specific wavelength and intensity, or generate heat.

This makes it possible to measure the target organism using chemotaxis of an organism that exhibits running performance or thermotaxis.

Therefore, the measurement device 2 can efficiently measure the target organism using the chemotaxis of an organism that exhibits running performance or thermotaxis.

In the measurement device 2 according to the present technology described above, the stimulus control unit 21 causes the stimulus generation device 3 to emit a specific substance.

This makes it possible to measure an organism that exhibits chemotaxis in response to the specific substance.

Therefore, the measurement device 2 can efficiently measure the target organism using the chemotaxis of an organism that exhibits chemotaxis in response to the specific substance.

The measurement system 1 according to the present technology described above includes the stimulus generation device 3 configured to output an external stimulus complying with a chemotaxis condition of an organism, the stimulus control unit 21 configured to cause the stimulus generation device 3 to generate the external stimulus, the imaging unit 14 configured to capture an image of a predetermined imaging range to which the external stimulus is output, and the measurement unit (class identification unit 23) configured to measure a target organism on the basis of the image captured by the imaging unit 14.

Also with such a measurement system 1, functions and effects similar to those provided by the measurement device 2 according to the present technology described above can be provided.

Note that the effects described in the present specification are merely examples and are not limitative, and other effects may be provided.

7. Present Technology

The present technology can also adopt the following configurations.

(1)

A measurement device including a stimulus control unit configured to cause a stimulus generation device to generate an external stimulus complying with a chemotaxis condition of an organism, an imaging unit configured to capture an image of a predetermined imaging range in which the external stimulus is generated, and a measurement unit configured to measure a target organism on the basis of the image captured by the imaging unit.

(2)

The measurement device according to (1), in which the imaging unit includes a vision sensor configured to asynchronously acquire pixel data in accordance with the amount of light incident on each of a plurality of pixels two-dimensionally arranged.

(3)

The measurement device according to (1) or (2), in which the stimulus control unit causes generation of the external stimulus by which the target organism exhibits positive chemotaxis.

(4)

The measurement device according to any of (1) to (3), in which the stimulus control unit causes generation of the external stimulus by which a non-target organism other than the target organism exhibits negative chemotaxis.

(5)

The measurement device according to (4), in which the stimulus control unit causes generation of the external stimulus by which a non-target organism other than the target organism exhibits negative chemotaxis and the target organism does not exhibit negative chemotaxis.

(6)

The measurement device according to (1) or (2), in which the stimulus control unit causes generation of the external stimulus by which the target organism dose not exhibit chemotaxis.

(7)

The measurement device according to (6), in which the external stimulus is light, and the stimulus control unit causes application of light by which the target organism does not exhibit chemotaxis.

(8)

The measurement device according to any of (1) to (7), in which the imaging unit captures an image while being moved along a predetermined direction.

(9)

The measurement device according to any of (1) to (8)

in which the measurement unit derives information based on a behavior performed by the target organism in exhibiting chemotaxis on the basis of the image captured by the imaging unit, and specifies the target organism on the basis of the information.

(10)

The measurement device according to (9), in which the measurement unit derives at least one of the number, the density, or the average activity level of the target organism.

(11)

The measurement device according to (2), in which the imaging unit includes the vision sensor and an imaging sensor configured to capture images at regular intervals in accordance with a frame rate.

(12)

The measurement device according to any of (1) to (11), in which the stimulus control unit causes the stimulus generation device to apply light having a specific wavelength and intensity, or generate heat.

(13)

The measurement device according to any of (1) to (12), in which the stimulus control unit causes the stimulus generation device to emit a specific substance.

(14)

A measurement method including causing a stimulus generation device to generate an external stimulus complying with a chemotaxis condition of an organism, capturing an image of a predetermined imaging range to which the external stimulus is output, and measuring a target organism on the basis of the captured image.

(15)

A measurement system including a stimulus generation device configured to generate an external stimulus complying with a chemotaxis condition of an organism, a stimulus control unit configured to cause the stimulus generation device to generate the external stimulus, an imaging unit configured to capture an image of a predetermined imaging range to which the external stimulus is output, and a measurement unit configured to measure the target organism on the basis of the image captured by the imaging unit.

REFERENCE SIGNS LIST

1 Measurement system
2 Measurement device
3 Stimulus generation device
10 Control unit
14 Imaging unit
**14*a*** Vision sensor
**14*b*** Imaging sensor
21 Stimulus control unit
22 Imaging control unit
23 Class identification unit

The invention claimed is:

1. A measurement device comprising:

circuitry configured to cause a stimulus generation device to generate an external stimulus complying with a chemotaxis condition of an organism in accordance with a predefined operation time chart that specifies a timing in minutes and a characteristic of the external stimulus, the operational time chart specifying application of the external stimulus for less than one hour;

capture an image of a predetermined imaging range in which the external stimulus is generated; and measure a target organism on a basis of the image captured, including movement of the target organism, wherein the operation time chart at least specifies increasing a wavelength of light applied by the stimulus generation device by a predetermined amount at predetermined minute intervals, and the external stimulus is generated by the stimulus generator in accordance with the increasing wavelength of light.

2. The measurement device according to claim 1, wherein the circuitry is further configured to asynchronously acquire pixel data in accordance with an amount of light incident on each of a plurality of pixels two-dimensionally arranged.

3. The measurement device according to claim 1, wherein the circuitry is further configured to cause generation of the external stimulus by which the target organism exhibits positive chemotaxis.

4. The measurement device according to claim 1, wherein the circuitry is further configured to cause generation of the external stimulus by which a non-target organism other than the target organism exhibits negative chemotaxis.

5. The measurement device according to claim 4, wherein the circuitry is further configured to cause generation of the external stimulus by which a non-target organism other than the target organism exhibits negative chemotaxis and the target organism does not exhibit negative chemotaxis.

6. The measurement device according to claim 1, wherein the circuitry is further configured to cause generation of the external stimulus by which the target organism does not exhibit chemotaxis.

7. The measurement device according to claim 6, wherein the external stimulus is light, and the circuitry is further configured to cause application of light by which the target organism does not exhibit chemotaxis.

8. The measurement device according to claim 1, wherein the circuitry is further configured to capture the image while being moved along a predetermined direction.

9. The measurement device according to claim 1, wherein the circuitry is further configured to derive information based on a behavior performed by the target organism in exhibiting chemotaxis on a basis of the image captured, and specifies the target organism on a basis of the information.

10. The measurement device according to claim 9, wherein the circuitry is further configured to derive at least one of the number, density, or average activity level of the target organism.

11. The measurement device according to claim 2, wherein the circuitry is further configured to capture images at regular intervals in accordance with a frame rate.

12. The measurement device according to claim 1, wherein the circuitry is further configured to cause the stimulus generation device to apply heat.

13. The measurement device according to claim 1, wherein the circuitry is further configured to cause the stimulus generation device to emit a specific substance.

14. A measurement method comprising:

causing a stimulus generation device to generate an external stimulus complying with a chemotaxis condition of an organism in accordance with a predefined operation time chart that specifies a timing in minutes and a characteristic of the external stimulus, the operational time chart specifying application of the external stimulus for less than one hour;

capturing an image of a predetermined imaging range to which the external stimulus is output; and measuring a target organism on a basis of the captured image, including movement of the target organism, wherein the operation time chart at least specifies increasing a wavelength of light applied by the stimulus generation device by a predetermined amount at predetermined minute intervals, and the external stimulus is generated in accordance with the increasing wavelength of light.

15. A measurement system comprising:

a stimulus generation device configured to generate an external stimulus complying with a chemotaxis condition of an organism; and circuitry configured to cause the stimulus generation device to generate the external stimulus in accordance with a predefined operation time chart that specifies a timing in minutes and a characteristic of the external stimulus, the operational time chart specifying application of the external stimulus for less than one hour;

capture an image of a predetermined imaging range to which the external stimulus is output; and measure the target organism on a basis of the image captured, wherein the operation time chart at least specifies increasing a wavelength of light applied by the stimulus generation device by a predetermined amount at predetermined minute intervals, and the external stimulus is generated in accordance with the increasing wavelength of light.

* * * * *